United States Patent
Otera et al.

[11] Patent Number: 4,745,229
[45] Date of Patent: May 17, 1988

[54] PROCESS FOR PREPARING α, β-UNSATURATED ALDEHYDES

[75] Inventors: Junzo Otera, Okayama; Shigeaki Suzuki; Takashi Onishi, both of Kitakanbara; Yoshiji Fujita, Kurashiki, all of Japan

[73] Assignee: Kuraray Company Ltd., Kurashiki, Japan

[21] Appl. No.: 15,095

[22] Filed: Feb. 13, 1987

[30] Foreign Application Priority Data

Feb. 28, 1986 [JP]  Japan ................................ 61-45104
Jun. 20, 1986 [JP]  Japan ............................... 61-145069

[51] Int. Cl.[4] ........................ C07C 45/56; C07C 45/27
[52] U.S. Cl. .................................. 568/490; 568/485; 568/488
[58] Field of Search ................ 568/488, 485, 490, 465

[56] References Cited

U.S. PATENT DOCUMENTS 3,157,703  11/1964  Franzen ............................ 568/490

FOREIGN PATENT DOCUMENTS 2432009   3/1980  France ............................. 568/426
1291246  10/1972  United Kingdom ................ 568/490

*Primary Examiner*—Werren B. Lone
*Attorney, Agent, or Firm*—Oblon, Fisher, Spivak, McClelland & Maier

[57] ABSTRACT

A process for preparing α,β-unsaturated aldehydes of the general formula (I)

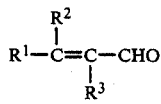

(I)

in which $R^1$, $R^2$ and $R^3$ are independently a hydrogen atom, or an alkyl or alkenyl group with or without being substituted with a lower acyloxy group. The aldehyde of the general formula (I) is prepared by reaction between an allylic chloride of the following general formula (IIa)

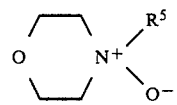

(IIa)

in which $R^1$, $R^2$ and $R^3$ have, respectively, the same meanings as defined above, and an amine oxide selected from the group consisting of tri(lower alkyl)amine N-oxides of the formula, $R_3^4 N^+ O^-$, in which $R^4$ represents a lower alkyl group having from 2 to 4 carbon atoms, and N-lower alkylmorpholine N-oxides of the following formula

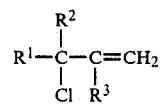

in which $R^5$ represents a lower alkyl group having from 1 to 4 carbon atoms. Alternatively, the aldehyde of the formula (I) is obtained by reaction between an allylic chloride of the following general formula (IIb)

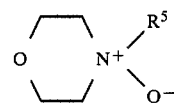

(IIb)

in which $R^1$, $R^2$ and $R^3$ have, respectively, the same meanings as defined above, and an amine oxide selected from the group consisting of tri(lower alkyl)amine N-oxides of the formula, $R_3^4 N^+ O^-$, in which $R^4$ has the same meaning as defined above, and N-lower alkylmorpholine N-oxides of the following formula

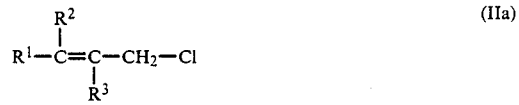

in which $R^5$ has the same meaning as defined above, in the presence of an alkali metal iodide or a copper halide.

18 Claims, No Drawings

PROCESS FOR PREPARING α,β-UNSATURATED ALDEHYDES

BACKGROUND OF THE INVENTION

1. Field of the Invention

This invention relates to a process for preparing α,β-unsaturated aldehydes of the general formula (I)

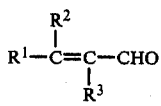
(I)

in which $R^1$, $R^2$ and $R^3$ are independently a hydrogen atom, or an alkyl or alkenyl group with or without being substituted with a lower acyloxy group. The α,β-unsaturated aldehydes of the general formula (I) prepared according to the process of the invention are useful as intermediates for preparing vitamin A used as a drug or a feed additive, or as fragrance chemicals.

2. Prior Art

α,β-Unsaturated aldehydes are known as prepared according to the following processes.

(1) A process of preparing 4-acetoxy-2-methyl-2-butenal which comprises reacting 4-chloro-3-methyl-2-butenyl acetate with dimethyl sulfoxide in the presence of dipotassium hydrogen phosphate, potassium dihydrogen phosphate and sodium bromide (The Journal of Organic Chemistry, Vol. 44, pp. 1716–1717 (1979)).

(2) A process of preparing 2,6-dimethyl-2,6-heptadienal in which 7-chloro-2,6-dimethyl-1,5-heptadiene is reacted with dimethylsulfoxide in the presence of silver tetrafluoroborate, and then triethylamine is added to the resulting reaction mixture (Tetrahedron Letters, pp. 917–920 (1974)).

(3) A process of preparing 3,7-dimethyl-2,6-octadienal by reaction between 1-chloro-3,7-dimethyl-2,6-octadiene and potassium 2-propanenitronate (British Pat. No. 1,291,246).

(4) A process of preparing 8-acetoxy-2,6-dimethyl-2,6-octadienal which comprises oxidizing 3,7-dimethyl-2,6-octadienyl acetate with selenium dioxide (Tetrahedron Letters, pp. 281–284 (1973)).

These prior art processes have problems from the standpoint of the industrial production of α,β-unsaturated aldehydes. More particularly, the process (1) requires the presence of a brominating agent and a buffering agent in the reaction system, thus requiring a plurality of reagents. Silver tetrafluoroborate used in large amounts on the process (2) is expensive. Potassium 2-propanenitronate used as an oxidizing agent in the process (3) is explosive and thus, care should be taken to its handling. Selenium dioxide used in the process (4) is toxic and sublimable, so that it has to be handled with great care. Accordingly, it is difficult to carry out the process (4) on an industrial scale.

SUMMARY OF THE INVENTION

An object of the invention is to provide a process for preparing unsaturated aldehydes of the general formula (I) from readily available industrial starting materials simply, inexpensively and in high yield.

According to the invention, there is provided a process for preparing α,β-unsaturated aldehydes of the general formula (I)

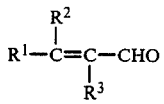
(I)

in which $R^1$, $R^2$ and $R^3$ are independently a hydrogen atom, or an alkyl or alkenyl group with or without being substituted with a lower acyloxy group, the process comprising either the step of reaction between an allylic chloride of the following general formula (IIa)

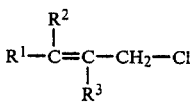
(IIa)

in which $R^1$, $R^2$ and $R^3$ have, respectively, the same meanings as defined above, and an amine oxide selected from the group consisting of tri(lower alkyl)amine N-oxides of the formula,

in which $R^4$ represents a lower alkyl group having from 2 to 4 carbon atoms, and N-lower alkylmorpholine N-oxides of the following formula

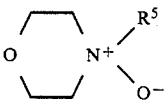

in which $R^5$ represents a lower alkyl group having from 1 to 4 carbon atoms, or the step of reaction between an allylic chloride of the following formula (IIb)

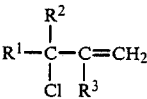
(IIb)

in which $R^1$, $R^2$ and $R^3$ have, respectively, the same meanings as defined above, and an amine oxide selected from the group consisting of tri(lower alkyl)amine N-oxides of the formula,

in which $R^4$ has the same meaning as defined above, and N-lower alkylmorpholine N-oxides of the following formula

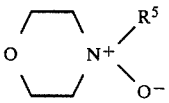

in which $R^5$ has the same meaning as defined above, in the presence of an alkali metal iodide or a copper halide.

Other objects, features and advantages of the invention will become apparent from the following description.

DETAILED DESCRIPTION AND EMBODIMENTS OF THE INVENTION

In the above general formulae (IIa) and (IIb), $R^1$, $R^2$ and $R^3$ are, respectively, as defined above, a hydrogen atom or an alkyl or alkenyl group which may be substituted with a lower acyloxy group. Examples of the alkyl group include a methyl group, an ethyl group, a propyl group, a 4-methylpentyl group and the like, and examples of the alkenyl group include a vinyl group, an allyl group, a 1-propenyl group, a 4-methyl-3-pentenyl group, a 4,8-dimethyl-3,7-nonadienyl group and the like. These alkyl or alkenyl groups may have a lower acyloxy group as a substituent. Examples of the lower acyloxy group include a formyloxy group, an acetoxy group, a propionyloxy group, a butyryloxy group and the like.

The alkyl group substituted with a lower acyloxy group may include, for example, an acetoxymethyl group, a 2-acetoxyethyl group and the like. Similarly, the alkenyl group substituted with a lower acyloxy group may include, for example, a 5-acetoxy-3-methyl-3-pentenyl group.

In the formula, $R_3^4N^+O^-$, which represents a tri(-lower alkyl)amine N-oxide used in the present invention, each $R^4$ is a lower alkyl group having from 2 to 4 carbon atoms, e.g. an ethyl group, a propyl group, an isopropyl group, a butyl group or the like. Examples of the tri(lower alkyl)amine N-oxide include triethylamine N-oxide, tri-n-propylamine N-oxide, tri-n-butylamine N-oxide and the like.

In the formula,

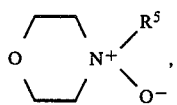

representing an N-lower alkylmorpholine N-oxide, $R^5$ represents a lower alkyl group having from 1 to 4 carbon atoms such as a methyl group, an ethyl group, a propyl group, an isopropyl group, a butyl group or the like. Examples of the N-lower alkylmorpholine N-oxide include N-methylmorpholine N-oxide, N-ethylmorpholine N-oxide, N-n-propylmorpholine N-oxide, N-n-butylmorpholine N-oxide and the like. If trimethylamine N-oxide is used for reaction with the allylic chloride of the general formula (IIa) or (IIb), an α,β-unsaturated aldehyde corresponding to the allylic chloride cannot be obtained in high yield as will be apparent from Comparative Examples 1 and 2 appearing hereinafter.

For the reaction of the invention, hydrates of amine oxides may also be used. Examples of such hydrates of amine oxides include N-methylmorpholine N-oxide monohydrate and the like. The amine oxides may be water-containing products having a water content of from about 5 to 50% on the weight basis. Preferably, the amine oxide is used in an amount of from about 1 to 5 moles per mole of the allylic chloride.

The process of the invention is particularly effective for the preparation of 8-acetoxy-2,6-dimethyl-2,6-octadienal using a compound of the formula (IIa) or (IIb) in which $R^1$ is a 5-acetoxy-3-methyl-3-pentenyl group, $R^2$ is a hydrogen atom and $R^3$ is a methyl group, citral using a compound of the formula (IIa) or (IIb) in which $R^1$ is a 4-methyl-3-pentenyl group, $R^2$ is a methyl group and $R^3$ is a hydrogen atom, farnesal using a compound of the general formula (IIa) or (IIb) in which $R^1$ is 4,8-dimethyl-3,7-octadienyl group, $R^2$ is a methyl group and $R^3$ is a hydrogen atom, 4-acetoxy-2-methyl-2-butenal using a compound of the formula (IIa) or (IIb) in which $R^1$ is an acetoxymethyl group, $R^2$ is a hydrogen atom and $R^3$ is a methyl group, and senecioaldehyde using a compound of the formula (IIa) or (IIb) in which $R^1$ is a methyl group, $R^2$ is a methyl group and $R^3$ is a hydrogen atom.

In order to obtain an aldehyde by oxidation of a corresponding chloride, there is known a process in which benzyl halides such as o-chlorobenzyl chloride, p-hydroxybenzyl chloride and the like are oxidized by reaction with triethylamine N-oxide (U.S. Pat. No. 4,335,052). The process of the invention is significantly improved over this known process with respect to the yield of an intended aldehyde. The results of our experiments in which benzyl chloride, which is a benzyl halide, is oxidized with triethylamine N-oxide reveal that the yield of benzaldehyde is not so high as will become apparent from Comparative Example 3 appearing hereinafter.

The alkali metal iodides include, for example, lithium iodide, sodium iodide, potassium iodide and the like. The amount of the alkali metal iodide if preferably from about 1 to about 3 moles per mole of the allylic chloride of the general formula (II). The copper halides may be, for example, copper (I) halides such as copper (I) chloride, copper (I) bromide, copper (I) iodide and the like, and copper (II) halides such as copper (II) chloride, copper (II) bromide and the like. The amount of the copper halide is generally from 0.001 to 2.0 moles, preferably from about 0.01 to 0.2 moles, per mole of the allylic chloride of the general formula (II). When the reaction is effected in the presence of a copper halide, it can be accelerated on co-existence of an alkali metal chloride such as lithium chloride, sodium chloride or potassium chloride in the reaction system. In this case, the alkali metal chloride is used in an amount of from about 0.1 to about 2 moles per mole of the allylic chloride of the general formula (II).

Although it is not essential to use a solvent for the reaction between the allylic chloride of the formula (IIa) or (IIb) and the amine oxide, solvents may be used for this purpose. Examples of such solvents include hydrocarbons such as benzene, toluene and the like; halogenated hydrocarbons such as dichloromethane, chloroform and the like; esters such as methyl acetate, ethyl acetate and the like; ethers such as diethyl ether, dioxane, tetrahydrofuran and the like; nitriles such as acetonitrile, propionitrile and the like; and amides such as N,N-dimethylformamide, N-methylpyrrolidone and the like. The amount of the solvent is preferably in the range of from about 1 to 10 ml per gram of the allylic chloride. The reaction temperature is favorably in the range of from about 20° to 80° C.

The thus obtained, α,β-unsaturated aldehyde of the general formula (I) is isolated and purified from the reaction mixture in the following manner.

Water is poured into the reaction mixture, followed by extraction with diethyl ether, hexane or ethyl acetate and removing the solvent from the extract by distillation. The resulting residue is purified by distillation or column chromatography, thereby obtaining the aldehyde of the general formula (I).

The allylic chloride of the general formula (IIa) may be readily prepared by a number of processes. Such processes include, for example, a process in which compounds having a 1,3-diene structure are reacted with hydrogen chloride (Japanese Laid-open Patent Application Nos. 50-160207 and 60-41623), a process in which compounds having a 1,3-diene structure are reacted with tert-butyl hypochlorite in the presence of a lower alkanoic acid (Journal of the Americal Chemical Society, Vol. 72, pp. 4608–4613), and a process in which compounds having a methylene group are reacted with trichloroisocyanuric acid or hypochlorous acid.

The allylic chloride of the general formula (IIb) can be prepared simply in the high yield by reaction of a corresponding olefinic compound with (i) hypochlorous acid in a two-phase system of a water-immiscible organic solvent and water or (ii) chlorinated isocyanuric acid or an alkali metal salt thereof.

The reaction in (i) above for the preparation of the allylic chloride of the general formula (IIb) is performed by adding dry ice to the two-phase system of an aqueous phase suspending bleaching powder or containing sodium hypochlorite and an organic phase dissolving the olefinic compound. Hypochlorous acid is formed in situ from bleaching powder or sodium hypochlorite and dry ice in the presence of water. The organic solvents are, for example, hydrocarbons such as hexane, benzene and the like; halogenated hydrocarbons such as dichloromethane, 1,2-dichloroethane and the like; ethers such as diethyl ether, diisopropyl ether and the like; and esters such as methyl acetate, ethyl acetate and the like. The amount of the organic solvent is preferably in the range of from about 5 to 50 ml per gram of the olefinic compound. When bleaching powder is used, the amount is preferably determined in such a way that calcium hypochlorite contained in the bleaching powder is in the range of about 0.4 to 0.7 moles per mole of the olefinic compound. In this case, the amount of water is preferably in the range of from 5 to 50 ml per gram of the bleaching powder. When, on the other hand, sodium hypochlorite is used, its amount is preferably in the range of from 0.8 to 1.2 moles per mole of the olefinic compound. For convenience' sake, a commercially available aqueous sodium hypochlorite solution having an active chlorine concentration of from 8.5 to 13.5% may be used, as it is, as the aqueous phase containing sodium hypochlorite. Dry ice may be used in amounts sufficient to convert a whole amount of calcium hypochlorite contained in bleaching powder or a whole amount of sodium hypochlorite into calcium carbonate or sodium hydrogen carbonate, but is preferred to be used in excess. The reaction temperature is favorably in the range of from about 0° to 15° C.

The reaction in (ii) mentioned before, which is a reaction between an olefinic compound and a chlorinated isocyanuric acid or its alkali metal salt, is described.

The chlorinated isocyanuric acid used in this reaction includes, for example, trichloroisocyanuric acid, dichloroisocyanuric acid and the like. The amount of the chlorinated isocyanuric acid or its alkali metal salt is preferably in the range of from about 0.3 to 0.6 moles for trichloroisocyanuric acid and from about 0.5 to 1.5 moles for dichloroisocyanuric acid, each per mole of an olefinic compound. The reaction between an olefinic compound and a chlorinated isocyanuric acid or its alkali metal salt may be effected in the presence or absence of an organic solvent. The solvents useful for this purpose include, for example, hydrocarbons such as hexane, benzene and the like; halogenated hydrocarbons such as dichloromethane, 1,2-dichloroethane and the like; esters such as ethyl acetate, methyl acetate and the like; and ketones such as acetone, ethyl methyl ketone and the like. The amount of the organic solvent is preferably in the range of from about 1 to 20 ml per gram of the olefinic compound. This reaction is preferably carried out at a temperature ranging from about −5° C. to 15° C.

The separation and purification of the thus obtained allylic compound of the general formula (IIb) from the reaction mixture is effected, for example, in the following manner. The reaction mixture is subjected to filtration, if necessary, to remove solid matters therefrom and poured into water or a saturated sodium sulfite aqueous solution, followed by extraction with diethyl ether, dichloromethane or hexane. The resulting extract is washed with a saturated sodium hydrogen carbonate aqueous solution and the solvent is distilled off from the solution to obtain a crude product of the allylic chloride of the general formula (IIb). The thus obtained crude product is subjected to distillation and/or column chromatography to obtain highly pure allylic chloride of the general formula (IIb). The allylic chloride of the general formula (IIb) used for the reaction with an amine oxide may be the above crude product.

The present invention is more particularly described by way of examples, which should not be construed as limiting the present invention.

EXAMPLE 1

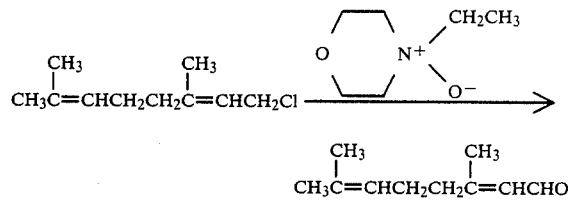

346 mg (2 mmols) of geranyl chloride and 787 mg (6 mmols) of N-ethylmorpholine N-oxide were placed in a flask, to which was further added 3 ml of N,N-dimethylformamide. The mixture was agitated at room temperature for 1 hour and at 50° C. for 4 hours. To the reaction mixture was added 10 ml of 2.5% sulfuric acid and 10 ml of ethyl acetate for phase separation. The resultant organic phase was washed with 5 ml of 2.5% sulfuric acid, 5 ml of a saturated sodium hydrogen carbonate aqueous solution and 5 ml of a 10% sodium sulfate aqueous solution successively, after which it was dried with magnesium sulfate. After the drying, the solvent was distilled off from the solution and the residue was subjected to distillation by the use of Kugelrohr distillation apparatus (bath temperature 93° C./3 Torr.) to obtain 268 mg (1.76 mmols) of citral. The yield was 88%.

EXAMPLES 2-3

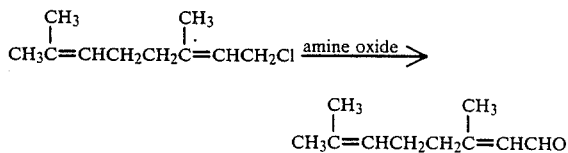

Example 1 was repeated except that instead of 787 mg (6 mmols) of N-ethylmorpholine N-oxide, there were used amine oxides in amounts indicated in Table 1, thereby obtaining citral. The results are shown in Table 1.

TABLE 1

| Example | Amine Oxides | Amount (mg) | Yield of Citral (%) |
|---|---|---|---|
| 2 | N—methylmorpholine N—oxide | 811 | 85 |
| 3 | triethylamine N—oxide (water content: 14%) | 816 | 90 |

EXAMPLES 4-7

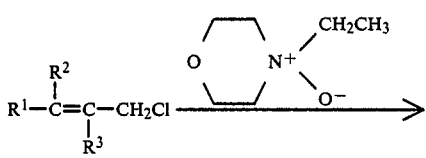

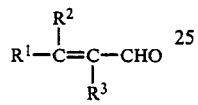

Example 1 was repeated except that there were used, instead of 346 mg (2 mmols) of geranyl chloride, predetermined amounts of allylic chlorides indicated in Table 2, thereby obtaining corresponding α,β-unsaturated aldehydes. The results are shown in Table 2.

TABLE 2

| Example | Allylic Chloride R$^1$ | R$^2$ | R$^3$ | Amount (mg) | Yield of α, β-Unsaturated Aldehyde (%) |
|---|---|---|---|---|---|
| 4 | (CH$_3$)$_2$C=CHCH$_2$CH$_2$C(CH$_3$)=CHCH$_2$CH$_2$— | CH$_3$ | H | 481 | 82* |
| 5 | CH$_3$COOCH$_2$— | H | CH$_3$ | 325 | 88* |
| 6 | CH$_3$CO$_2$CH$_2$CH=C(CH$_3$)CH$_2$CH$_2$— | H | CH$_3$ | 231 | 90* |
| 7 | CH$_3$ | CH$_3$ | H | 209 | 85 |

Note:
*Separation of the respective α, β-unsaturated aldehydes was effected by a column chromatography using silica gel.

EXAMPLE 8

(a) Preparation of a mixture of 4-chloro-3-methylenebutyl acetate and 4-chloro-3-methyl-1-2-butenyl acetate

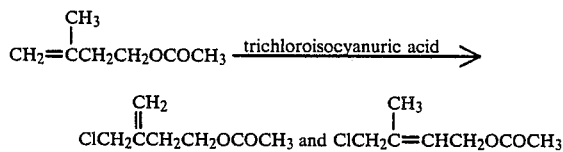

1.28 g (10 mmols) of 3-methyl-3-butenyl acetate and 10 ml of ethyl acetate were placed in a flask. While cooling the flask in an ice bath, 1.16 g (5 mmols) of trichlorosiocyanuric acid was added. After completion of the addition, the ice bath was removed and the mixture was continuedly agitated at room temperature for 10 hours. 100 ml of hexane was added to the reaction mixture and the resulting precipitate was removed by filtration through a glass filter having silica gel thereon. The filtrate was concentrated under reduced pressure and the resultant concentrate was subjected to distillation by the use of Kugel-rohr distillation apparatus (bath temperature: 140° to 160° C./20 Torr.), thereby obtaining 0.92 g of a colorless oily substance.

This oily substance was subjected to an NNR analysis, revealing that is was a mixture of 4-chloro-3-methylenebutyl acetate and 4-chloro-3-methyl-2-butenyl acetate (at a mixing ratio of 65:35). The yield was 57%.

4-Chloro-3-methylenebutyl acetate:
NMR (hexamethyldisiloxane/CDCl$_3$)δ: 2.00 (s, 3H), 2.46 (t, J=6.7 Hz, 2H), 4.04 (s, 2H), 4.18 (t, J=6.7 Hz, 2H), 4.98 (m, 1H), 5.17 (s, 1H).

4-Chloro-3-methyl-2-butenyl acetate:
NMR (hexamethyldisiloxane/CDCl$_3$)δ: 1.77 (s, 3H), 2.00 (s, 3H), 3.96 (s, 2H), 4.58 (d, J=6.9 Hz, 2H), 5.64 (t, J=6.9 Hz, 1H).

(b) Preparation of a mixture of 4-acetoxy-2-methylene butanal and 4-acetoxy-2-methyl-2-butenal ClCH$_2$C(=CH$_2$)CH$_2$CH$_2$OCOCH$_3$ and

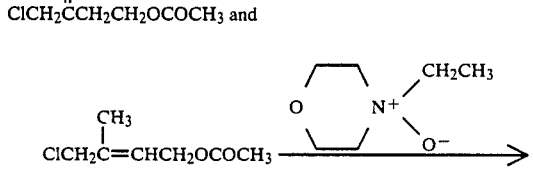

ClCH$_2$C(CH$_3$)=CHCH$_2$OCOCH$_3$

O=CHC(=CH$_2$)CH$_2$CH$_2$OCOCH$_3$ and O=CHC(CH$_3$)=CHCH$_2$OCOCH$_3$

Example 1 was repeated except that there was used, instead of 346 mg (2 mmols) of geranyl chloride, 325 mg (2 mmols) of a mixture of 4-chloro-3-methylenebutyl acetate obtained in (a) of Example 8 and having a ratio of 65:35, thereby obtaining 231 mg of a light yellow oily substance. Kugel-rohr distillation apparatus was used for distillation of the products (bath temperature 100° to 130° C./4 Torr).

This oily substance was subjected to the NMR analysis, revealing that it was a mixture of 4-acetoxy-2-methylenebutanal and 4-acetoxy-2-methyl-2-butenal at a mixing ratio of 70:30. The yield was found to be 81%.
4-Acetoxy-2-methylenebutanal:

NMR (hexamethyldisiloxane/CDCl$_3$)δ: 1.98 (s, 3H), 2.33–2.60 (m, 2H), 4.05–4.23 (m, 2H), 6.04 (s, 1H), 6.31 (s, 1H), 9.53 (s, 1H).

4-Acetoxy-2-methyl-2-butenal:

NMR (hexamethyldisiloxane/CDCl$_3$)δ: 1.77 (d, 3H), 2.07 (s, 3H), 4.86 (d, J=6 Hz, 2H), 6.47 (m, 1H), 9.45 (s, 1H).

EXAMPLE 9

(a) Preparation of 6-Chloro-3,7-dimethyl-2,7-octadienyl acetate

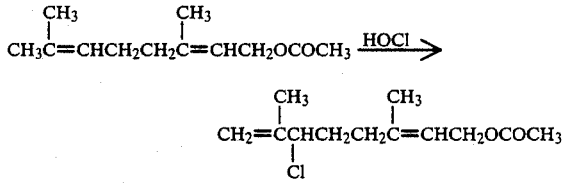

15.70 g (80.0 mmols) of 3,7-dimethyl-2,6-octadienyl acetate, 200 ml of dichloromethane and 46.0 ml (81.4 mmols of sodium hypochlorite) of a sodium hypochlorite aqueous solution (1.77 mols/liter) were placed in a flask. 10.2 g of dry ice was added, portion by portion, to the mixture in 1 hour. During the addition, the flask was cooled on an ice bath, by which the inner temperature was maintained at 10° C. or below. After completion of the addition of dry ice, the reaction mixture was agitated at 4° C. for 1 hour. 100 ml of water was added to the reaction mixture and the organic phase was separated. The aqueous phase was extracted with 100 ml of dichloromethane. The organic phase was combined with the extract, followed by washing with 100 ml of a 10% sodium sulfite aqueous solution and drying with magnesium sulfate. The solvent was distilled off, thereby obtaining 18.3 g of a crude product of 6-chloro-3,7-dimethyl-2,7-octadienyl acetate. According to the NMR analysis, it was demonstrated that the purity of 6-chloro-3,7-dimethyl-2,7-octadienyl acetate in the crude product was 80%. Yield: 79%.

Part of the crude product was purified by column chromatography using silica gel [eluent: hexane/ethyl acetate (ratio by volume)=1/9-1/3] to isolate 6-chloro-3,7-dimethyl-2,7-octadienyl acetate. This acetate was subjected to instrumental analysis with the following results.

NMR (hexamethyldisiloxane/CDCl$_3$)δ: 1.63 (s, 3H), 1.75 (s, 3H), 2.00 (s, 7H), 4.27 (m, 1H), 4.53 (d, J=7 Hz, 2H), 4.85 (m, 1H), 4.97 (s, 1H), 5.33 (t, J=7 Hz, 1H).

IR (film) ν: 1725 (C=O), 895 (CH$_2$=C) cm$^{-1}$.

FI-MS m/e (relative intensity): 232 (18, M$^+$), 230 (100, M$^+$), 194 (58, M$^+$—HCl).

(b) Preparation of 8-acetoxy-2,6-dimethyl-2,6-octadienal

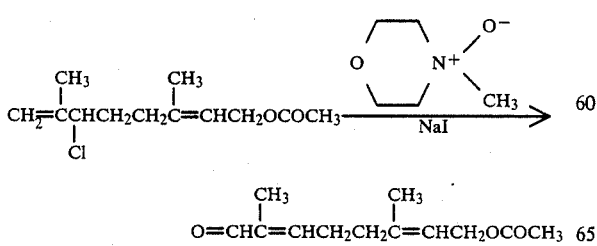

1.15 g (3.99 mmols) of 6-chloro-3,7-dimethyl-2,7-octadienyl acetate (purity: 80%), 0.91 g (6 mmols) of sodium iodide and 1.36 g (10 mmols) of N-methylmorpholine N-oxide (monohydrate) were placed in a flask, to which was added 5 ml of N,N-dimethylformamide. The mixture was agitated at 50° C. for 4 hours. After completion of the reaction, 10 ml of water was added to the reaction mixture, followed by extraction twice each with 70 ml of diethyl ether. The resulting extract was washed with each 20 ml of 3% sulfuric acid, a saturated sodium hydrogen carbonate aqueous solution and a 10% sodium sulfite aqueous solution, and dried with magnesium sulfate. After drying, the solvent was removed by distillation from the solution and the resulting residue was purified by column chromatography using silica gel [eluent: ethyl acetate/hexane (volume by ratio)=1/9-1/3], thereby obtaining 0.627 g of 8-acetoxy-2,6-dimethyl-2,6-octadienal. Yield: 75%. The results of an instrumental analysis of the 8-acetoxy-2,6-dimethyl-2,6-octadienal are as follows.

NMR (hexamethyldisiloxane/CDCl$_3$)δ: 1.67 (m, 6H), 1.93–2.77 (m, 7H), 4.53 (d, J=7 Hz, 2H), 5.40 (m, 1H), 6.40 (m, 1H), 9.37 , 10.11 (s, 1H in combination).

IR (film) ν: 2700 (CHO), 1720 (C=O), 1670 (C=O) cm$^{-1}$.

FI-MS m/e (relative intensity): 210 (100, M$^+$), 211 (23, M$^+$+1), 150 (18, M$^+$—CH$_3$CO$_2$H).

EXAMPLES 10–13

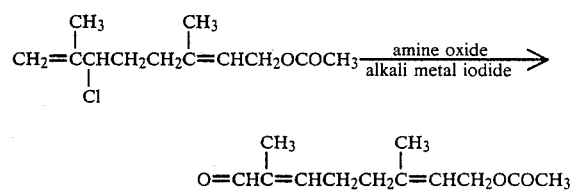

Example 9(b) was repeated except that there were used, instead of 0.91 g (6.0 mmols) of sodium iodide and 1.36 g (10.0 mmols) of N-methylmorpholine N-oxide, alkali metal iodides and amine oxides indicated in Table 3, thereby obtaining 8-acetoxy-2,6-dimethyl-2,6-octadienal. The results are shown in Table 3.

TABLE 3

| Example | Alkali Metal | Amount (g) | Amine Oxide | Amount (g) | Yield of 8-Acetoxy-2,6-dimethyl-2,6-octadienal (%) |
|---|---|---|---|---|---|
| 10 | lithium iodide | 1.07 | N—methylmorpholine N—oxide | 2.04 | 62 |
| 11 | potassium iodide | 0.80 | N—methylmorpholine N—oxide | 2.04 | 52 |
| 12 | lithium iodide | 1.07 | N—ethylmorpholine N—oxide | 1.38 | 65 |
| 13 | lithium iodide | 1.07 | Triethylamine N—oxide | 1.40 | 52 |

EXAMPLE 14

(a) Preparation of 6-Chloro-3,7-dimethyl-2,7-octadienyl acetate

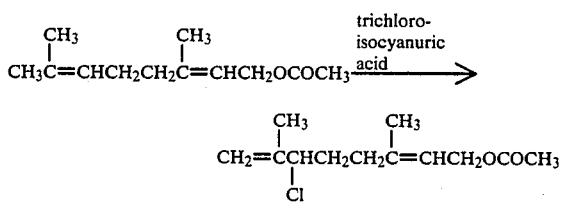

19.6 g (0.10 mols) of 3,7-dimethyl-2,6-octadienyl acetate and 60 ml of hexane were placed in a flask, to which 10.07 g (0.043 mols) of trichloroisocyanuric acid was added at intervals of 5 minutes by division into five portions. During the addition, the flask was cooled so that the inner temperature was maintained at 5° C. or below. After completion of the addition, the reaction solution was agitated at 5° C. for 15 hours. The resultant solution was subjected to removal of a solid matter by filtration and the solid matter was washed three times each with 50 ml of hexane. The filtrate was combined with the washings, followed by washing successively with each 50 ml of a 10% sodium sulfite aqueous solution, a 2% sodium carbonate aqueous solution and a saturated sodium chloride aqueous solution and drying with magnesium sulfate. The solvent was removed from the solution by distillation, thereby obtaining 21.10 g of a crude product of 6-chloro-3,7-dimethyl-2,7-octadienyl acetate. The NMR analysis revealed that a purity of 6-chloro-3,7-dimethyl-2,7-octadienyl acetate in the crude product was 92%. Yield: 84%.

(b) Preparation of 8-acetoxy-2,6-dimethyl-2,6-octadienal of the mixture at 50° C. for 10 hours. 40 ml of water was added to the reaction mixture, after which it was extracted twice each with 70 ml of diethyl ether. The resultant extract was successively washed with each 20 ml of 3% sulfuric acid, a saturated sodium hydrogen carbonate aqueous solution and a saturated ammonium chloride aqueous solution, and dried with magnesium sulfate. The solvent was distilled off from the solution and the resultant residue was purified by column chromatography using silica gel [eluent: ethyl acetate/hexane (ratio by volume)=1/9-1/3], thereby obtaining 1.21 g of 8-acetoxy-2,6-dimethyl-2,6-octadienal. Yield: 61%. The results of the instrumental analysis were found to be substantially coincident with those obtained in Example 9(b).

EXAMPLES 15–21

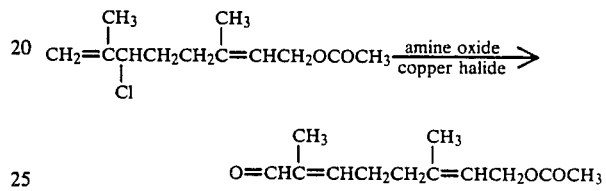

Example 14(b) was repeated except that there was used, instead of 92 mg (0.92 mmols) of copper(I) chloride, 3.65 g (29.6 mmols) of triethylamine N-oxide and 5 ml of dioxane, copper halides, amine oxides and solvents indicated in Table 4, thereby obtaining 8-acetoxy-2,6-dimethyl-2,6-octadienal. The results are shown in Table 4 below.

TABLE 4

| Example | Copper Halide | Amount (mg) | Amine Oxide | Amount (g) | Solvent | Amount (ml) | Yield of 8-Acetoxy-2,6-dimethyl-2,6-octadienal (%) |
|---|---|---|---|---|---|---|---|
| 15 | copper(I) chloride | 95 | triethylamine N—oxide | 3.65 | benzene | 4.5 | 55 |
| 16 | copper(I) chloride | 91 | triethylamine N—oxide | 3.65 | N,N—dimethylformamide | 4.5 | 53 |
| 17 | copper(I) bromide | 125 | triethylamine N—oxide | 3.65 | dioxane | 5.0 | 59 |
| 18 | copper(I) iodide | 170 | triethylamine N—oxide | 3.65 | dioxane | 5.0 | 52 |
| 19 | copper(I) chloride | 40 | N—methylmorpholine N—oxide (monohydrate) | 2.70 | chloroform | 10 | 51 |
| 20 | copper(II) chloride | 67 | N—methylmorpholine N—oxide (monohydrate) | 2.70 | chloroform | 10 | 47 |
| 21 | copper(II) bromide | 110 | N—methylmorpholine N—oxide (monohydrate) | 2.70 | chloroform | 10 | 53 |

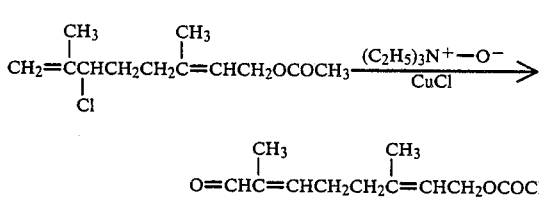

2.36 g (9.41 mmols) of 6-chloro-3,7-dimethyl-2,7-octadienyl acetate (purity: 92%), 92 mg (0.93 mmols) of copper(I) chloride and 3.65 g (29.6 mmols) of triethylamine N-oxide (purity: 95%) were placed in a flask, to which 5 ml of dioxane was added, followed by agitation

EXAMPLE 22

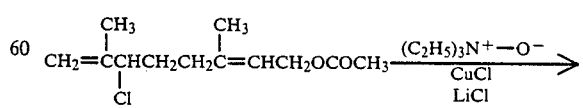

Example 14(b) was repeated except that 42 mg (0.99 mmols) of lithium chloride was further added to the reaction mixture and the reaction time was changed to 7 hours, thereby obtaining 1.23 g of 8-acetoxy-2,6-dimethyl-2,6-octadienal. Yield: 62%. The results of the instrumental analysis of the product were substantially conicident with those obtained in Example 14(b).

EXAMPLE 23

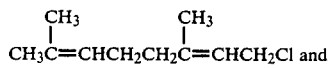

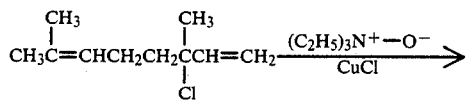

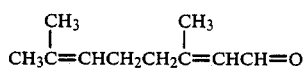

330 mg (1.9 mmols) of a mixture of gernayl chloride, neryl chloride and linalyl chloride (ratios=61:32:7), 24.3 mg (0.25 mmols) of copper(I) chloride, 0.82 g (6.0 mmols) of triethylamine N-oxide (water content of 14%), and 3 ml of N,N-dimethylformamide were mixed and agitated at 45° C. for 2 hours. 15 ml of ethyl acetate and 8 ml of 2% sulfuric acid were added to the mixture and shaked sufficiently to extract an organic matter. The organic phase was collected, to which 145 mg of n-tetradecane was added, followed by subjecting to gas chromatography. As a result, it was found that starting geranyl chloride, neryl chloride and linalyl chloride disappeared with citral being formed at a yield of 67%.

COMPARATIVE EXAMPLE 1

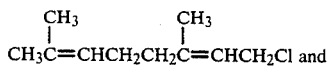

Example 1 was repeated except that there was used 0.67 g (6 mmols) of trimethylamine N-oxide (dihydrate) instead of 787 mg (6 mmols) of N-ethylmorpholine N-oxide, thereby obtaining citral at a yield of 55%.

COMPARATIVE EXAMPLE 2

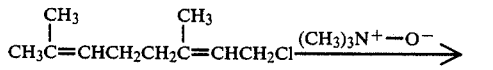

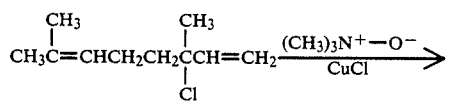

Example 23 was repeated using 0.67 g (6 mmols) of trimethylamine N-oxide (dihydrate) instead of 0.82 g (6 mmols) of triethylamine N-oxide (water content of 14%), thereby obtaining citral at a yield of 40%.

COMPARATIVE EXAMPLE 3

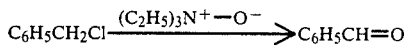

302 mg (2.4 mmols) of benzyl chloride and 0.82 g (6 mmols) of triethylamine N-oxide were dissolved in 3 ml of N,N-dimethylformamide, and the solution was agitated at 75° C. for 4 hours. 15 ml of ethyl acetate and 8 ml of 2% sulfuric acid were added to the reaction mixture, which was shaked sufficiently and separated into the respective phases. 155.5 mg of n-dodecane was added to the organic phase, followed by gas chromatography, revealing that the benzyl chloride disappeared with the benzaldehyde being formed at a yield of 69%.

What is claimed is:

1. A process for preparing an α,β-unsaturated aldehyde of the formula:

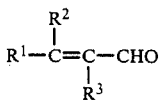

in which $R^1$, $R^2$ and $R^3$ are, independently, a hydrogen atom, or an alkyl or alkenyl group with or without being substituted with a lower acyloxy group, comprising the steps of:

(i) reacting (a) an allylic chloride of the formula

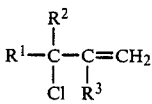

in which $R^1$, $R^2$ and $R^3$ have, respectively, the same meanings as defined above, and (b) about 1–5 moles per mole of said allylic chloride of an amine oxide selected from the group consisting of tri(lower alkyl)amine N-oxides of the formula $R_3^4N^+O^-$, in which $R^4$ is a $C_{2-4}$ alkyl group, and N-lower alkylmorpholine N-oxides of the formula

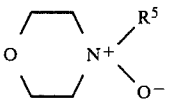

in which $R^5$ is a $C_{1-4}$ alkyl group; at a temperature from 20°–80° C. in the presence of about 1–3 moles per mole of said allylic chloride of an alkali metal iodide of from about 0.001–2.0 moles per mole of said allylic chloride of a copper halide.

2. The process of claim 1, wherein $R^1$ is a 5-acetoxy-3-methyl-3-pentenyl group, $R^2$ is a hydrogen atom, and $R^3$ is a methyl group.

3. The process of claim 1, wherein $R^1$ is a 4-methyl-3-pentenyl group, $R^2$ is a methyl group, and $R^3$ is a hydrogen atom.

4. The process of claim 1, wherein $R^1$ is a 4,8-dimethyl-3,7-octadienyl group, $R^2$ is a methyl group, and $R^3$ is a hydrogen atom.

5. The process of claim 1, wherein $R^1$ is an acetoxymethyl group, $R^2$ is a hydrogen atom, and $R^3$ is a methyl group.

6. The process of claim 1, wherein $R^1$ is a methyl group, $R^2$ is a methyl group, and $R^3$ is a hydrogen atom.

7. The process of claim 1, wherein said alkali metal iodide is a member selected from the group consisting of lithium iodide, sodium iodide and potassium iodide.

8. The Process of claim 1, wherein said copper halide is a member selected from the group consisting of copper(I) chloride, copper(II) chloride, copper(I) bromide, copper(II) bromide and copper(I) iodide.

9. The process of claim 1, wherein said reacting step is carried out in the presence of a solvent.

10. The process of claim 9, wherein said solvent is present in an amount from about 1-10 ml per gram of said allylic chloride.

11. A process for preparing an $\alpha,\beta$-unsaturated aldehyde of the formula:

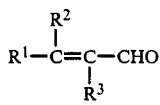

in which $R^1$, $R^2$ and $R^3$ are, independently, a hydrogen atom, or an alkyl or alkenyl group with or without being substituted with a lower acyloxy group, comprising the steps of:

(i) reacting (a) an allylic chloride of the formula

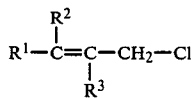

in which $R^1$, $R^2$ and $R^3$ have, respectively, the same meanings as defined above, and (b) about 1-5 moles per mole of said allylic chloride of an amine oxide selected from the group consisting of tri(lower alkyl)amine N-oxides of the formula

in which $R^4$ is a $C_{2-4}$ alkyl group, and N-lower alkylmorpholine N-oxides of the formula

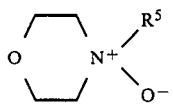

in which $R^5$ is a $C_{1-4}$ alkyl group; at a temperature from 20°-80° C.

12. The process of claim 11, wherein $R^1$ is a 5-acetoxy-3-methyl-3-pentenyl group, $R^2$ is a hydrogen atom, and $R^3$ is a methyl group.

13. The process of claim 11, wherein $R^1$ is a 4-methyl-3-pentenyl group, $R^2$ is a methyl group, and $R^3$ is a hydrogen atom.

14. The process of claim 11, wherein $R^1$ is a 4,8-dimethyl-3,7-octadienyl group, $R^2$ is a methyl group, and $R^3$ is a hydrogen atom.

15. The process of claim 11, wherein $R^1$ is an acetoxymethyl group, $R^2$ is a hydrogen atom, and $R^3$ is a methyl group.

16. The process of claim 11, wherein $R^1$ is a methyl group, $R^2$ is a methyl group, and $R^3$ is a hydrogen atom.

17. The process of claim 14, wherein said reacting step is carried out in the presence of a solvent.

18. The process of claim 17, wherein said solvent is present in an amount from about 1-10 ml per gram of said allylic chloride.

* * * * *